United States Patent [19]

Rich

[11] Patent Number: 5,693,944

[45] Date of Patent: *Dec. 2, 1997

[54] GAS ANALYZER CUVETTES

[75] Inventor: David R. Rich, Glastonbury, Conn.

[73] Assignee: NTC Technology, Inc., Wilmington, Del.

[*] Notice: The term of this patent shall not extend beyond the expiration date of Pat. No. 5,616,923.

[21] Appl. No.: 300,146

[22] Filed: Sep. 2, 1994

[51] Int. Cl.[6] .................................................. G01N 21/61
[52] U.S. Cl. .......................................................... 250/343
[58] Field of Search ................................. 250/343, 338.5

[56] References Cited

U.S. PATENT DOCUMENTS

5,067,492  11/1991  Yelderman et al. ........................ 128/719
5,296,706  3/1994  Braig et al. ............................... 250/343

*Primary Examiner*—Carolyn E. Fields
*Attorney, Agent, or Firm*—Hughes, Multer & Schacht

[57] ABSTRACT

Gas analyzer systems which include: (1) a transducer for outputting a signal indicative of the concentration of a specified gas in a sample which may contain that gas, and (2) an airway adapter or cuvette with a flow passage for confining the sample to a particular path traversing the transducer. The cuvettes feature radiant energy transmitting windows which are flush mounted in apertures on opposite sides of the cuvette flow passage and are fabricated from a polymer such as biaxially oriented polypropylene which is malleable, yet resistant to wrinkling, warping, and other forms of distortion. Retainer rings keep the windows flat and distortion free with an accurately reproducible spacing between the windows.

19 Claims, 8 Drawing Sheets

GAS ANALYZER CUVETTES

TECHNICAL FIELD OF THE INVENTION

The present invention relates to novel, improved cuvettes; to methods for manufacturing those devices; and to novel, improved gas analyzers employing the cuvettes.

DEFINITIONS

Cuvette: a device which is configured to contain a static or dynamic gas sample and in which the concentration of a designated gas in the sample can be ascertained.

Sampling Passage: a cavity in a cuvette which confines a sample composed of one or more gases to a particular flow path traversed by an optical flow path between an infrared radiation emitter and an infrared radiation detector (dynamic sample) or to a particular location along a flow path of that character (static sample).

BACKGROUND OF THE INVENTION

U.S. Pat. Nos. 4,859,858 and 4,859,859 were issued to Knodle et al. on 22 Aug. 1989; and U.S. Pat. No. 5,153,436 was issued to Apperson et al. on 6 Oct. 1992. These three patents disclose analyzers for outputting a signal indicative of the concentration of a designated gas in a sample being monitored by the apparatus.

The gas analyzers disclosed in the '858, '859, and '436 patents are of the non-dispersive type. They operate on the premise that the concentration of a designated gas can be measured by: (1) passing a beam of infrared radiation through the gas, and (2) then ascertaining the attenuated level of the energy in a narrow band absorbable by the designated gas. This is done with a detector capable of generating a concentration proportional electrical output signal.

One important application of the invention at the present time is monitoring the level of carbon dioxide in the breath of a medical patient. This is typically done during a surgical procedure as an indication to the anesthesiologist of the patient's condition, for example. As the patient's wellbeing, and even his life, is at stake, it is of paramount importance that the carbon dioxide concentration be measured with great accuracy.

In a typical instrument or system employing non-dispersive infrared radiation to measure gas concentration, including those disclosed in the '858, '859, and '436 patents, the infrared radiation is emitted from a source and focused into a beam by a mirror. The beam is propagated through a sample of the gases being analyzed. After passing through the body of gases, the beam of infrared radiation passes through a filter. That filter reflects all of the radiation except for that in a narrow band centered on a frequency which is absorbed by the gas of concern. This narrow band of radiation is transmitted to a detector which produces an electrical output signal proportional in magnitude to the magnitude of the infrared radiation impinging upon it. Thus, the radiation in the band passed by the filter is attenuated to an extent which is proportional to the concentration of the designated gas. The strength of the signal generated by the detector is consequently inversely proportional to the concentration of the designated gas and can be inverted to provide a signal indicative of that concentration.

In a typical medical application of the gas analyzers just described, a cuvette is employed to sample a patient's gas exchange via a nasal cannula or to connect an endotracheal tube to the plumbing of a mechanical ventilator. The cuvette confines expired and inspired gases to a specific flow path; and it furnishes an optical path between an infrared radiation emitter and an infrared radiation detector unit, both components of a transducer which can be detachably coupled to the cuvette.

A typical cuvette is molded from an appropriate polymer, and it has a passage defining the flow path for the gases being monitored. The optical path traverses the flow path with apertures in the wall of the cuvette and aligned along and on opposite sides of the flow passage allowing the beam of infrared radiation to enter the cuvette; traverse the gases in the flow passage; and, after being attenuated, exit from the cuvette to the filter and radiation detector. Transmissive sapphire windows in the apertures confine the gases to the cuvette flow passage and keep out foreign matter while minimizing the loss of infrared energy as the beam enters and exits from the cuvette.

Sapphire is a relatively expensive material. Consequently, cuvettes of the character just described are invariably cleaned, sterilized, and reused. The cleaning and sterilization of a cuvette is time-consuming and inconvenient; and the reuse of a cuvette may be perceived as posing a significant risk, especially if the cuvette was previously employed in monitoring a patient suffering from an infectious disease. Another disadvantage of using sapphire windows is that adhesive bonding is the only viable technique for mounting the windows to the cuvette. This technique is slow and expensive, and care must be taken that the windows are accurately positioned.

Efforts have been made to reduce the cost of cuvettes by replacing the sapphire cuvette windows with windows fabricated from a variety of polymers. These efforts have heretofore been unsuccessful.

One, if not the major, problem encountered in replacing sapphire cuvette windows with windows fabricated from a polymer is that of establishing and maintaining a precise optical path length through the sample being analyzed. This is attributable to such factors as a lack of dimensional stability in the polymeric material, the inability to eliminate wrinkles, and the lack of a system for retaining the windows at precise locations along the optical path.

One proposal for solving this problem is made in U.S. Pat. No. 5,067,492 issued 26 Nov. 1991 to Yelderman et al. The patented approach is to squeeze the cuvette between two housing segments of the transducer with which it is used in the course of assembling the cuvette to the transducer. If the same transducer is employed and if its housing is dimensionally stable, this will in theory ensure that the distance between the two cuvette windows is the same each time the same cuvette is used.

This solution has major drawbacks. Squeezing the cuvette is apt to wrinkle or otherwise distort the perhaps initially not distortion-free plastic windows; and this may affect the transmittance of the windows enough to cause a significant error in the concentration of the gas being monitored. Furthermore, in the Yelderman et al. design, the windows are spaced inwardly from the flow passage-associated ends of the optical path apertures. This leaves cavities communicating with the flow passage in which unwanted debris can collect; and these crevices can adversely affect the flow of gases through the cuvette. Also, the structure employed to position and retain the plastic windows in the body of the cuvette is important; and Yelderman et al. contains only the sketchiest of suggestions of how this might be accomplished, let alone a description of a window retaining system that would minimize wrinkles and other distortions and accurately hold the windows in place, particularly considering the squeezing of the cuvette needed to assemble the cuvette to its adapter. Another problem with the Yelderman et al. hardware is that of assembling the cuvette to the adapter because of the interference fit between these two components.

SUMMARY OF THE INVENTION

Now invented and disclosed herein are new and novel cuvettes which can be manufactured cheap enough that it is practical to dispose of them after use with a single patient or if the cuvette becomes unusable due to contamination or a dirty window, for example. At the same time, those novel cuvettes are free of the defects and drawbacks of previously proposed cuvettes with sapphire-substitute windows including the one disclosed in the above-cited Yelderman et al. patent.

The cuvettes disclosed herein resemble those heretofore proposed to the extent that they include a flow passage for the gas(es) being monitored, apertures to and from the flow passage for transferring infrared radiation propagated along an optical path traversing the gases in the flow passage, and radiation transmitting windows in those apertures for confining the gas(es) to the flow passage. However, the cuvettes of the present invention differ from those heretofore proposed in a number of important respects.

One is the material from which the windows are fabricated. The conventional polyethylenes and polypropylenes heretofore proposed by Yelderman et al. and others is inherently not very strong in the thicknesses required for acceptable infrared transmission. As a result of this lack of strength, such windows will stretch and move when exposed to the changes in airway pressure inherent in breathing circuits. The resulting changes in pathlength naturally cause variations in system calibration and accuracy. Additionally, such windows are very susceptible to damage in the course of normal handling and installation in the breathing circuit.

Instead of the conventional polymers employed by Yelderman et al., the windows of the novel cuvettes disclosed herein are preferably fabricated from a malleable homopolymer, most preferably a biaxially oriented polypropylene (BOPP), in the thickness range of 0.001 in to 0.005 in. Polymers of this character are widely available, strong in thin gauges, malleable, and relatively transparent to infrared radiation; and much better control over the thickness of the film can be obtained.

BOPP offers numerous advantages. The high strength of BOPP allows the windows to be self-supporting and sufficiently rigid to eliminate the need to secondarily define the pathlength with the sensor in order to prevent movement with changes in airway pressure (In the preferred embodiment described in Yelderman et al., "portions of the gas analyzer housing protrude and slightly squeeze the optical windows of the adapter body so as to accurately locate the optical windows . . . so that the membranes of the optical windows are a predetermined distance from each other").

BOPP is sufficiently strong to maintain, without relaxation, the tension imparted during assembly to produce a flat, distortion-free window. Also, BOPP windows are more durable and less apt to be damaged and rendered unusable in normal use. BOPP films are sufficiently strong to withstand the stresses of the mechanical installation and retention. By the nature of the manufacturing process for BOPP films, thickness variations are minimized, thus providing improved reproducibility of the pathlength and less variability in the optical properties.

Because BOPP's are inexpensive, it is practical to dispose of cuvettes with windows fabricated from these materials after a single use or if the cuvette should become dirty, contaminated, or otherwise unusable without cleaning, disinfection, and the like.

A zero calibration can be performed on the transducer after the cuvette is assembled to it. This calibration is important because it allows one to achieve optimum accuracy by zeroing out spectral tolerances in the window material. This eliminates errors which might otherwise be caused by deviations from nominal tolerances in the lot-to-lot chemical composition as well as thickness and other physical specifications of the stock material.

Another advantage of the present invention is that the polymeric materials from which the windows are formed are also, by virtue of their biaxial polymer chain orientation, resistant to wrinkling, warping, and other forms of accuracy-affecting distortion. Yet they are malleable, which makes the material easy to form to a shape in which they span and seal the apertures in the cuvette.

Yet another advantage of employing the preferred polymeric window materials is that cuvettes with windows formed from those materials are backwards compatible. That is, cuvettes with windows fabricated from such materials can be substituted for cuvettes with sapphire windows without redesigning the transducers with which the cuvettes are used.

Another significant feature of the present invention is the mounting of the windows with their inner faces flush with that surface of the cuvette bounding the flow passage. This eliminates debris trapping and flow affecting nooks and crannies such as those in the Yelderman et al. cuvettes.

Still another important feature of the present invention is the use of skeletal snap-in retainers or rings to immobilize the windows at precise locations in the cuvette bodies. These retainers can also be employed to collapse the window-forming material around those components as they are installed. This provides gastight seals between the retainers and the body of the cuvette. At the same type, this novel technique for installing and sealing the cuvette windows eliminates the need to heat the windows if heat sealing were employed. This is important as heat could well ruin the optical flatness required for accurate carbon dioxide measurement.

Other advantages attributable to the snap ring system employed to hold the windows in place are:

(1) fast, reliable, inexpensive manufacture of the adapters is promoted;
(2) adhesives and the attendant requirements for careful handling, dispensing, and curing are eliminated;
(3) heat sealing is not required;
(4) the adapter body can be molded from high strength polymers which have better dimensional stability than the conventional polyethylenes and polypropylenes employed by Yelderman et al. as the adapter body and the windows do not have to be fabricated from similar material.

The apertures in the cuvettes are configured to precisely locate the windows along the gas traversing optical path; and the cuvette is fabricated from a rigid, deformation resistant material. As a result the length of the optical path can be depended upon to remain constant within the very close tolerances required for accurate measurement without employing the Yelderman et al. cuvette squeezing assembly technique or another equally inconvenient method of providing an accurate optical path length.

The cuvette apertures are also configured to provide the just-discussed snap-in assembly of the window retainers to the body of the cuvette and eliminate the need for heat sealing or adhesives.

The inner, flow passage-associated ends of the cuvettes are preferably so dimensioned that a window or retainer can not pass through the aperture if it is accidentally dislodged. This is a significant safety feature as it keeps a dislodged retainer or window from perhaps passing to a mechanical ventilator or other equipment or, even worse, being pumped through an endotracheal tube into a patient's lungs.

The objects, advantages, and features of the present invention will be apparent to the reader from the foregoing and the appended claims and as the ensuing detailed description and discussion proceeds in conjunction with the accompanying drawing.

DETAILED DESCRIPTION OF THE INVENTION

Figures 1, 5, 6:
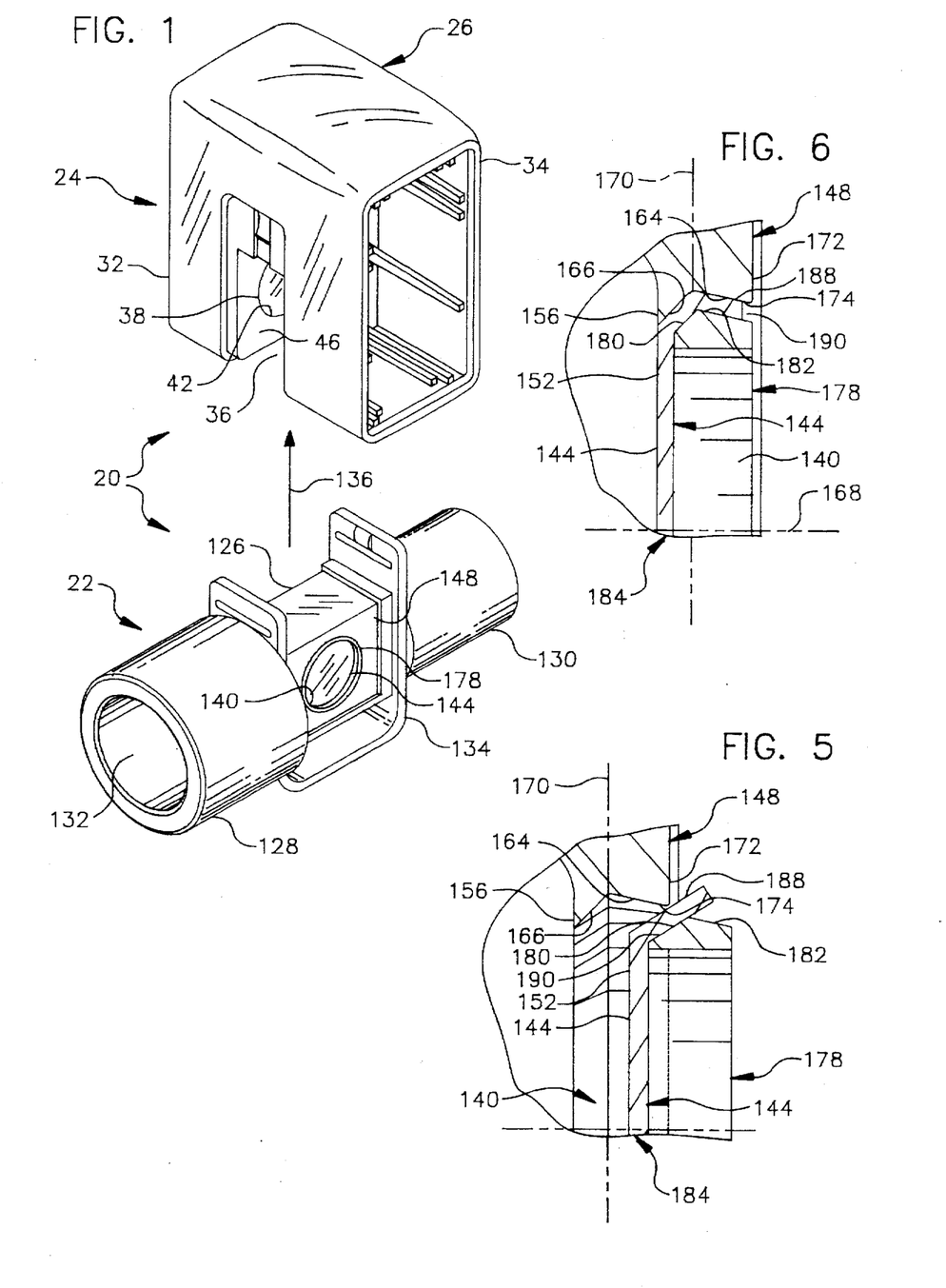
FIG. 1 is an exploded view of a gas analyzer comprising: (a) an airway adapter type of cuvette which embodies the principles of the present invention and which provides a particularized flow path for a gas being analyzed, and (b) a transducer which generates a beam of infrared radiation, propagates that beam along an optical path traversing the cuvette flow path, detects the beam as attenuated by a designated gas in the flow path, and outputs a signal indicative of the concentration of the designated gas.
FIG. 5 is a fragmentary section through the airway adapter showing one of its radiation transmitting windows in an initial stage of being installed with the technique depicted in FIG. 3 and the machine illustrated in FIG. 4.
FIG. 6 is a view like FIG. 5 but showing the window completely installed.
Figure 2:
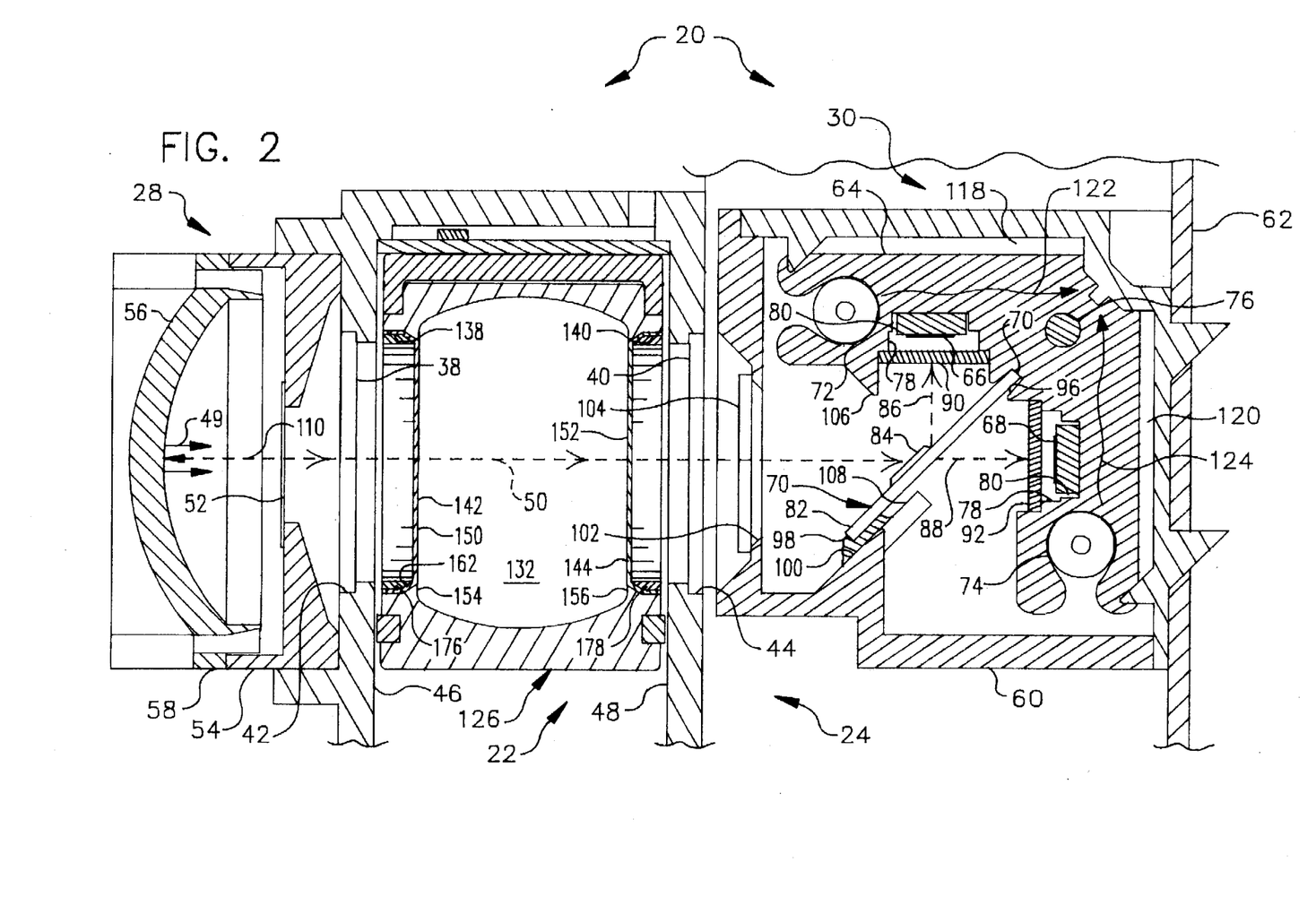
FIG. 2 is a section through the airway adapter/transducer assembly.

Referring now the drawing, FIGS. 1 and 2 depict a gas analyzer 20 composed of: (1) an airway adapter 22 embodying the principles of the present invention and designed for connection between an endotracheal tube inserted in a patient's trachea and the plumbing of a mechanical ventilator; and (2) a complementary transducer 24 for outputting: (a) a signal proportional in magnitude to the concentration of carbon dioxide flowing through airway adapter 20, and (b) a reference signal. These signals can be ratioed in the manner disclosed in the above-cited '858, '859, and '436 patents to provide a third signal accurately and dynamically representing the concentration of the carbon dioxide flowing through the airway adapter.

FIG. 1 shows primarily the polymeric housing 26 of transducer 24. The transducer also includes an infrared radiation emitter unit or source 28 and a detector unit 30 (see FIG. 2).

That casing 26 of transducer 24 in which the infrared radiation emitter unit 28 and detector unit 30 are housed has first and second end sections 32 and 34 with a rectangularly configured gap 36 therebetween. With the transducer assembled to airway adapter 22, the two sections 32 and 34 of transducer casing 26 embrace airway adapter 22, integrating the adapter and transducer into a single, easily handled unit or assembly.

Optically transparent windows 38 and 40 are installed in transversely aligned apertures 42 and 44 provided in the inner end walls 46 and 48 of transducer housing 26. These windows allow the beam 49 of infrared radiation generated in unit 28 in the left-hand end section 32 of transducer housing 26 to pass along optical path 50 to airway adapter 22 and from the airway adapter to the detector unit 30 in the right-hand section 34 of the transducer housing. At the same time, windows 38 and 40 keep gases from escaping and keep foreign material from penetrating to the interior of the transducer casing.

Unit 28 is employed to emit infrared radiation, to form that energy into beam 49, and to propagate the beam along the optical path 50 traversing the gas being monitored as it flows through airway adapter 22. Unit 20 includes: (1) a thick film infrared radiation emitter 52, (2) an emitter protecting cap 54, (3) a parabolic, gold-over-copper-plated mirror 56 for collating the energy outputted from emitter 52, and (4) an emitter-, mirror-, and cap-supporting base 58.

Detector unit 30 includes a boxlike housing 60 mounted on a printed circuit board 62. A monolithic, heat conductive, isothermal support 64 is installed in housing 60. Supported from and mounted in support 64 are: (1) data and reference detectors 66 and 68, (2) a beam splitter 70, (3) detector heaters 72 and 74, and (4) a thermistor-type current flow-limiting device 76. The system in which heaters 72 and 74 and thermistor device 76 are incorporated (see above-cited U.S. Pat. No. 5,153,436) is employed to keep the reference and data detectors 68 and 66 at the same, selected temperature, typically with a tolerance of not more than 0.01° C.

Detectors 66 and 68 are preferably fabricated with lead selenide detector elements because of the sensitivity which that material possesses to electromagnetic energy having wavelengths which are apt to be of interest.

Each of the two detectors 66 and 68 is mounted in a stepped recess 78 opening onto the front side of heat conductive support 64. A gap 80 around the periphery of the detector and between the detector and isothermal support 64 electrically isolates the detector from the also conductive, isothermal support.

Beam splitter 70 has a generally parallelepipedal configuration. This component is fabricated from a material such as silicon or sapphire which is essentially transparent to electromagnetic energy with wavelengths of interest. The exposed front surface 82 of the beam splitter is covered with a coating 84 which will reflect to data detector 66 as indicated by arrow 86 in FIG. 2 energy having a wavelength longer than about 4 microns. The energy of shorter wavelengths is, instead, transmitted through the beam splitter to reference detector 68 as is suggested by arrow 88 in the same figure.

Bandpass filters 90 and 92 limit the electromagnetic energy respectively reflected from and transmitted by beam splitter 70 and impinging upon detectors 66 and 68 to energy in selected bandwidths. Reference detector filter 92 in detector unit 30 is centered on a wavelength of 3.681 μm and has a half power bandwidth of 0.190 μm. The data detector bandpass filter 90 is centered on a wavelength of 4.260 μm and has a bandwidth of 0.10 μm. This is two times narrower than the band passed by filter 92. The carbon dioxide absorption curve is fairly narrow and strong, and bandpass filter 90 centers the transmission band within that absorption curve. Therefore, if there is a change in carbon dioxide level in the gas(es) being analyzed, the maximum modulation for a given change in carbon dioxide level is obtained.

Each of the bandpass filters 90 and 92 is installed in that stepped recess 78 in monolithic, isothermal support 64 in which the associated detector 66 or 68 is mounted.

The upper edge 94 of beam splitter 70 is fitted into a recess 96 in monolithic, isothermal support 64 midway between the bandpass filter 90 in front of data detector 66 and the bandpass filter 92 in front of reference detector 68. The opposite, lower part 98 of the beam splitter is fixed to an inclined, integral lip 100 which extends inwardly from detector unit casing 60.

The electromagnetic energy in beam 49 reaches beam splitter 70 through an aperture 102 in the front side of detector unit casing 60. A sapphire window 104 spans aperture 102 and keeps foreign material from penetrating to the interior of housing 60.

To exclude extraneous energy, and thereby ensure that only the energy in beam 49 reaches beam splitter 70, light traps 106 and 108 are provided. The first of these is a triangularly sectioned, inwardly extending projection of monolithic isothermal support 64. The second, cooperating light trap 108 is aligned with, fixed in any convenient fashion to, and extends inwardly from the casing-associated ledge 100 supporting beam splitter 70.

The operation of transducer 24 is believed to be apparent from the drawings and the foregoing, detailed description of the transducer. Briefly, however, electromagnetic energy in the infrared portion of the spectrum is generated by heating the source or emitter 52 of emitter unit 28, preferably by applying bipolar pulses of electrical energy to the emitter unit. The energy thus emitted is propagated toward the concave, emitter unit mirror 56 as shown by arrow 110 in FIG. 2. Mirror 56 collimates and focuses this energy and propagates it in the form of beam 49 along optical path 50 across the gas(es) flowing through airway adapter 22.

Energy in a species specific band is absorbed by the gas of interest flowing through the airway adapter (typically carbon dioxide) to an extent proportional to the concentration of that gas. Thereafter, the attenuated beam passes through the aperture 102 in detector unit casing 60, is intercepted by beam splitter 70, and is either reflected toward data detector 66 or transmitted to reference detector 68. The bandpass filters 90 and 92 in front of those detectors limit the energy reaching them to specified (and different) bands. Each of the detectors 66 and 68 thereupon outputs an electrical signal proportional in magnitude to the intensity of the energy striking that detector. These signals are amplified and then ratioed to generate a third signal accurately reflecting the concentration of the gas being monitored. The signal processor used for this purpose is independent of airway adapter 22 and transducer 24, is not part of the present invention, and will accordingly not be disclosed herein.

Resistance heaters 72 and 74 and thermistor 76 are installed in isothermal support 64, producing efficient, conductive heat transfer between the heaters and the support. The spatial relationship between heater 72 and data detector 66 and between heater 74 and reference detector 68 are identical, and the spatial relationship between thermistor 76 and each of the heaters 72 and 74 is also identical. Furthermore, the two heaters 72 and 74 are so located with respect to the associated detectors 66 and 68 that the thermal energy emitted from the heaters travels first across the detectors and then across the current flow-limiting thermistor 76 to heat dumps provided by gaps 118 and 120 between isothermal support 64 and detector unit housing 60 (The heat flow paths are identified by arrows 122 and 124 in FIG. 2). As a consequence of the foregoing and the high thermal conductivity of isothermal support 64, the data and reference detectors 66 and 68 can readily be maintained at the same temperature as is required for accuracy of gas concentration measurement.

Figure 3:
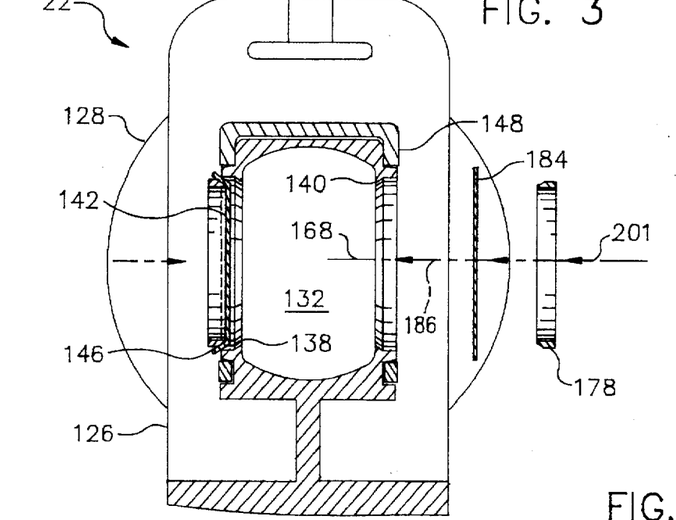
FIG. 3 is an exploded view comprised of: a transverse section through the airway adapter; one of two windows which transmit infrared radiation to the airway adapter flow passage and, after it has been attenuated by the designated gas, from the flow passage to the exterior of the airway adapter; and a retainer which holds the window in place in the body of the airway adapter.

Referring more specifically to FIGS. 1–3, airway adapter 22 embodies the principles of the present invention and is typically molded from a polycarbonate or a comparable rigid, dimensionally stable polymer. The airway adapter has a generally parallelepipedal center section 126 and two cylindrical end sections 128 and 130 with a sampling (or flow) passage 132 extending from end-to-end through the adapter. Left-hand and right-hand airway adapter end sections 128 and 130 are axially aligned with center section 126.

The central section 126 of airway adapter 22 provides a seat for transducer 24. An integral, U-shaped casing element 134 positively locates transducer 24 endwise of the adapter and, also, in that transverse direction indicated by arrow 136 in FIG. 1. That arrow also shows the direction in which airway adapter 22 is displaced to detachably assemble it to transducer 24. The airway adapter snaps into place (see the above-cited '858 and '859 patents); no tools are needed to assemble or remove the adapter.

Apertures 138 and 140 are formed in the center section 126 of airway adapter 22. With transducer 24 assembled to the airway adapter, these apertures are aligned along optical path 50. Thus, infrared radiation beam 49 can travel from the infrared radiation emitter unit 28 in transducer 24 transversely through airway adapter 22 and the gas(es) flowing through airway adapter flow passage 132 to the infrared radiation detector unit 30 of transducer 24.

To: (a) keep the gases flowing through airway adapter sampling passage 132 from escaping through apertures 138 and 140 without attenuating the infrared radiation traversing optical path 50, and (b) keep foreign material from the interior of the airway adapter, the apertures 138 and 140 are sealed by windows 142 and 144 which have a high transmittance for radiation in the infrared portion of the electromagnetic spectrum.

As discussed above, that casing 26 of transducer 24 in which the source unit 28 and detector unit 30 are housed has first and second end sections 32 and 34 with a rectangularly configured gap 36 therebetween. With the transducer assembled to airway adapter 22, the two sections 32 and 34 of transducer casing 26 embrace those two inner side walls 146 and 148 of airway adapter central section 126 in which energy transmitting windows 142 and 144 are installed. This securely attaches airway adapter 22 to transducer 24 with airway adapter windows 142 and 144 and transducer windows 38 and 40 all aligned along optical pathway 50, allowing infrared radiation beam 49 to travel from emitter unit 28 to detector unit 30 through the gas(es) in sampling passage 132.

Heretofore, the windows of cuvettes such as that shown in FIGS. 1–3 as well as cuvettes of other configurations have been fabricated from sapphire because of that material's favorable optical properties; stability; and resistance to breakage, scratching, and other forms of damage. However, as discussed above, sapphire windows are expensive; and this makes it impractical to discard the cuvette after it is used to monitor a single patient. Instead, the cuvette must be cleaned, sterilized, and reused, which is inconvenient and often perceptually hazardous.

It has now been found that the cost of manufacturing a cuvette can be reduced—even to the point of making it practical to dispose of the cuvette after a single use—by fabricating the cuvette windows from an appropriate polymer rather than the many times more expensive, heretofore employed sapphire.

It is essential to accuracy that the polymer transmit a usable part of the infrared radiation impinging upon it. As discussed above, the preferred window material is biaxially oriented polypropylene.

Referring now specifically to FIGS. 3, 5, and 6, windows 142 and 144 are installed in airway adapter apertures 138 and 140 such that the inner surfaces 150 and 152 of the windows are flush with the inner surfaces 154 and 156 of airway adapter center section side walls 146 and 148. This eliminates any recesses in optical path apertures 138 and 140 in which debris might collect and obscure the optical aperture. The flush-mounting also minimizes flow resistance and assures that there are no edges which would interfere with the delivery of medication or the introduction of catheters or other cannula through the airway adapter.

The perimeters 162 and 164 of the two window-receiving apertures 138 and 140 have a configuration which is designed to position the energy transmitting window 142 or 144 in its aperture 138 or 140 with the window in the above-discussed flush relationship with the inner surface (154 or 156) of the airway adapter side wall in which the aperture is formed. Aperture 140 is typical. The perimeter 164 of aperture 140, which is shown to an enlarged scale in FIGS. 5 and 6, has an inner segment 166. That segment tapers inwardly (toward the centerline 168 of aperture) from: (1) a plane 170 lying between and parallel to the inner and outer surfaces 156 and 172 of airway adapter side wall 160, to (2) the inner side wall surface 156. A second, integral segment 174 of the aperture tapers inwardly (also toward aperture centerline 168) over that span lying between plane 170 and outer side wall surface 172.

Windows 142 and 144 are held in place (or immobilized) in the associated apertures 138 and 140 in the flush-mounted relationship just described with skeletal, elastically compressible, snap-in retainer rings 176 and 178, which are typically made from brass. Brass has the advantage that it is cheap, easily machined, and readily plated with other metals such as nickel, if desired. However, other materials may be employed in place of brass although many polymers are not suitable as they would not be able to withstand the forces generated during the installation of the retainers.

The two retainers 176 and 178 are identical; accordingly, only retainer 178, best shown in FIGS. 5 and 6, will be described in detail. That airway adapter component has a circular configuration. Its periphery has a first, inner segment 180 which complements the inner segment 166 of window aperture perimeter 164; like the latter, it is tapered toward aperture centerline 168 from plane 170 to airway adapter inner side wall surface 156. The ring also has an integral, outer segment 182 complementing the outer segment 174 of the aperture 140 perimeter. That retainer ring segment tapers toward aperture centerline 168 from plane 170 to airway adapter side wall outer surface 174.

By virtue of the complementary configurations just described, retainer ring 176 snaps into aperture 140. It is thereby positively retained in that exact location shown in FIG. 6 in which it retains window 144 in aperture 140 in the flush relationship to airway adapter inner wall surface 156 described above.

Referring now most specifically to FIGS. 3, 5, and 6, the initial step in installing window 144 is to die cut or otherwise form a circular blank 184 from an appropriately thick sheet of the selected infrared radiation transmitting polymer. As shown in FIG. 3, blank 184 and retainer ring 176 are positioned adjacent airway adapter side wall 160 in axial alignment with and centered along the centerline 168 of aperture 140. The blank and retainer ring are then displaced toward airway adapter 22 and into aperture 140 as indicated by arrow 186 in FIG. 3. As blank 184 and retainer ring 176 are forced through aperture 140 toward sampling passage 132, the margin 188 of blank 184—particularly if the blank is made from a malleable polymer as is preferred—is molded first around the inner segment 180 of retainer ring 178 (see FIG. 5) and then around the outer segment 182 of the retainer ring (see FIG. 6). This results in the marginal segment 188 of the blank forming a gastight seal in the gap 190 between the perimeter 164 of aperture 140 and the periphery of retainer ring 178 when the blank and retainer ring reach the assembled, or final, FIG. 6 position. At the same time, the rigidity and toughness of the material and the just described installation process result in the window segment 140 of the blank being placed under tension and therefore being flat and free of distortions which might produce an error in the signal outputted by transducer 24.

Figure 4:
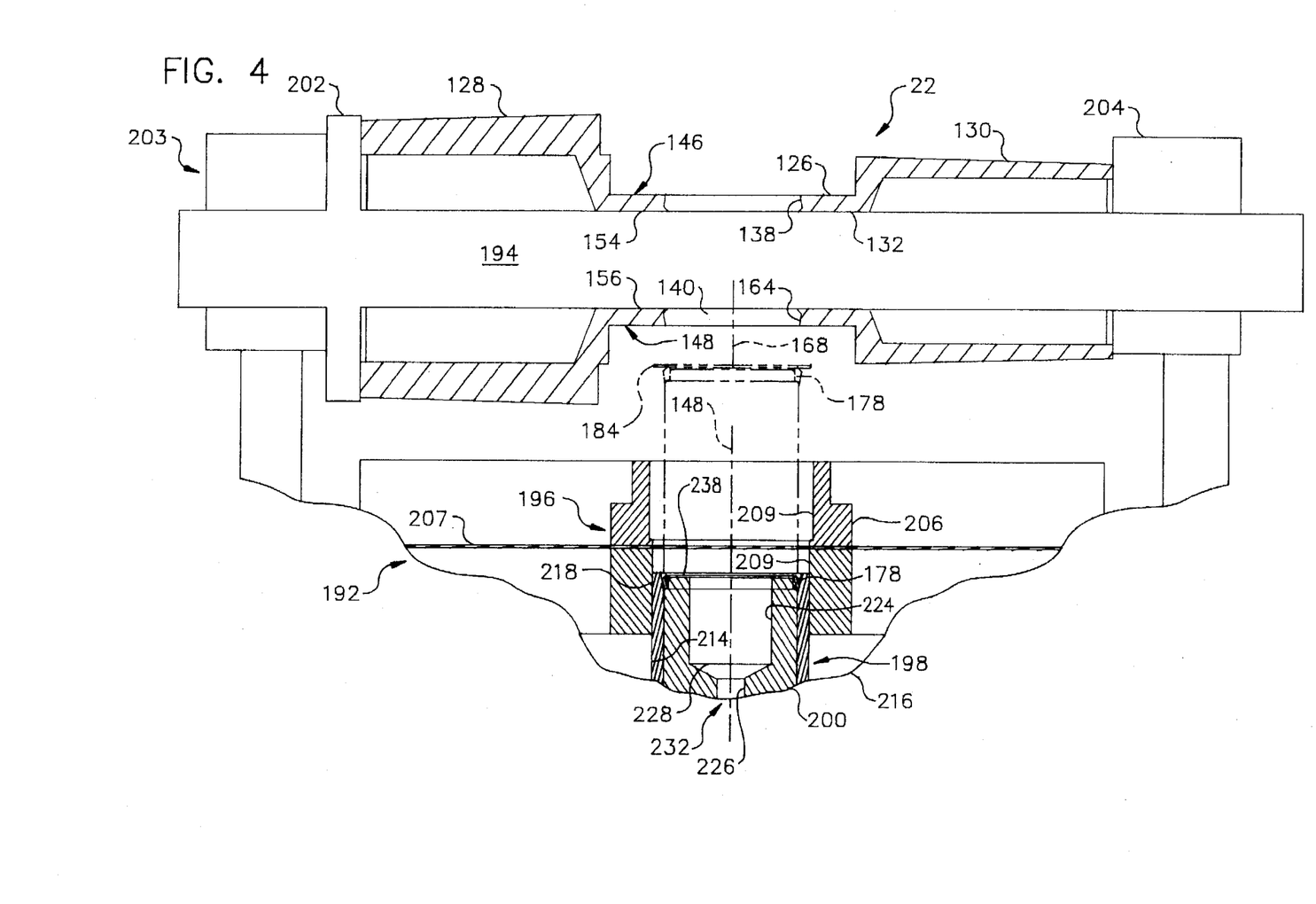
FIG. 4 is a simplified view of one machine that can be used to install the windows and retainers in the airway adapter of FIG. 1 and to seal the gaps between the retainers and the apertures in which they are installed.
Figure 11:
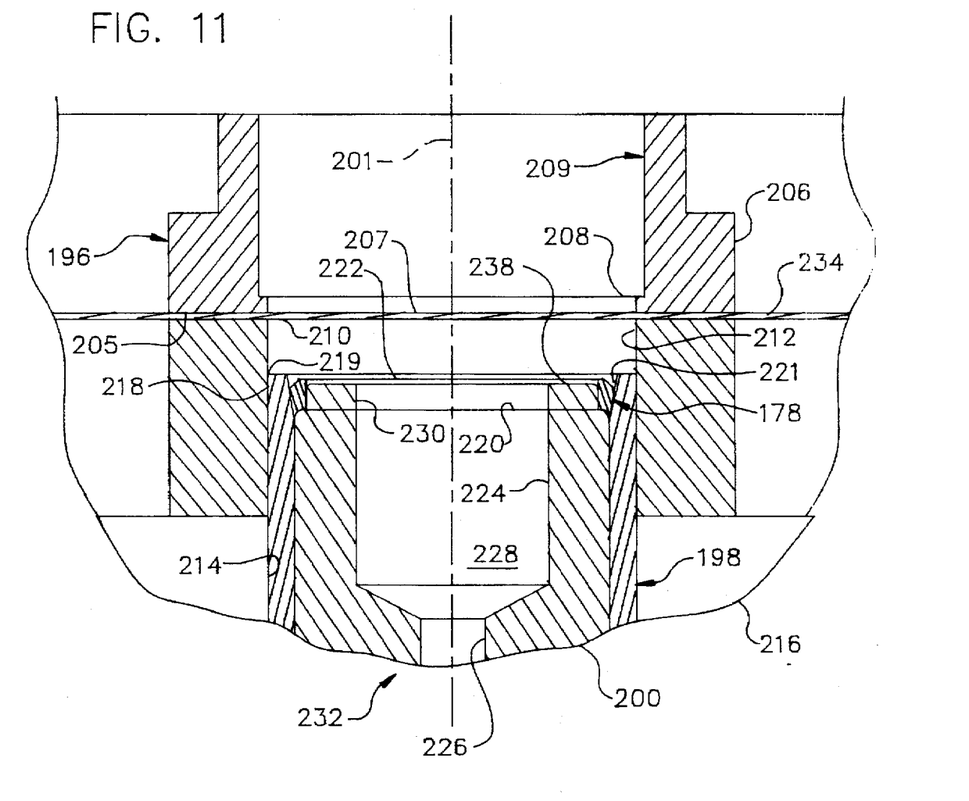
FIG. 11 is a fragment of FIG. 4 to an enlarged scale.

One machine for forming blank 184 and for so pressing that blank and retainer ring 178 into aperture 140 as to form and immobilize window 144 with the retainer ring snapped into place and the gap 190 between it and the perimeter 164 of aperture 140 sealed is illustrated in FIGS. 4 and 11 and identified by reference character 192. That machine includes an airway adapter-supporting mandrel 194, a die 196, and a hollow punch 198 supported by a second mandrel 200 for movement in the arrow 186 and opposite directions (the same machine is of course used to form and install window 142 and retainer ring 176).

Airway adapter-supporting mandrel 194 is dimensioned and configured to match the sampling passage 132 through airway adapter 22. This mandrel is employed to position the airway adapter with aperture centerline 168 in axial alignment with the longitudinal centerline 201 of die 196 and punch 198. The mandrel also backs up the side wall 148 of the airway adapter as the window forming blank 184 and retainer ring 178 are pressed into the aperture.

Mandrel 200 is mounted to machine framework 203. An integral annular stop 202 and a frame-associated stop 204 immobilize airway adapter 22 in the illustrated and just described window installation position relative to punch 196.

Die 196 is a hollow, stationary, cylindrical component mounted along centerline 198 and operationally located adjacent the airway adapter 22 in which windows are being installed. A slot 205 extending through the wall 206 of the die at right angles to centerline 198 accommodates a rectilinearly displaceable strip 207 of window-forming polymer. An integral, annular ledge 208 extending inwardly from die wall 206 into longitudinally extending central bore 209 immediately above slot 205 defines one of two cooperating cutting edges 210 for severing blank 184 from strip 207. The second cutting edge is formed on punch 198 and is described below.

Mandrel-supported, hollow punch 198 is an elongated tube. It is dimensioned for a free sliding fit in: (1) the lower segment 212 of the longitudinally extending bore 209 through die 196, and (2) an axially aligned bore 214 through a stationary, punch-and-die supporting component 216 of machine 192. The die-associated end segment 218 of punch 198 is tapered outwardly to complement the configuration of retaining ring peripheral outer segment 182. The sharp cutting edge 219 at the free end of punch segment 218 cooperates with the cutting edge 210 of die 196 to sever blank 184 from strip 207 as punch 198 is displaced relative to die 196 in the arrow 186 direction.

Punch-supporting mandrel 200 is fixed in any appropriate fashion to tubular punch 198 and is displaced in the arrow 186 and opposite directions by a mechanism which has not been shown as it is not part of the present invention. The die facing end 220 of mandrel 200 lies inwardly from the cutting edge 219 of punch 198. This leaves an open recess or cavity 221 for retainer 178. The upper edge 222 of the retainer lies below cutting edge 219 and will not interfere with the cutting blank 184 from strip 206.

Mandrel 200 has a vacuum system including a central cavity 224 opening onto the die facing end 220 of the mandrel and an internal vacuum line 226 providing fluid communication between cavity 224 and a vacuum pump (not shown). A porous plug 228, fitted into vacuum cavity 224, promotes a uniform negative pressure profile at the die-facing end of cavity 224 and, consequently, a similarly uniform negative pressure profile over the area of the hollow bore 230 through retainer ring 178.

The vacuum system just described and identified in its totality by reference character 232 is employed to hold the window-forming blank 184 on and in axial alignment with the retaining ring 178 installed in cavity 221 as punch 198 and the retaining ring 178 are displaced further in the arrow 186 direction to press the blank and retaining ring into aperture 140.

Installation machine 192 is shown in FIG. 4 at the beginning of its operating cycle with retainer ring 178 having been placed in cavity 221 from the open upper end of the bore 209 in die 196 by dropping it through that bore, the hole 234 left by punching the preceding blank from strip 207, and the lower part 212 of die bore 209, care being taken to ensure that the retainer ring is placed in recess 221 in the orientation shown in FIG. 4. Thus installed in recess 221, retainer ring 178 is seated on the upper end 220 of mandrel 200 and backed against deformation during the installation process. The upper edge 222 of the retainer lies in the recessed, non-interfering relationship with the cutting edge 184 of punch 198. A protruding, annular, hollow boss 238 at the upper end 220 of die 196 centers retainer ring 178 about axial centerline 201, precisely aligning the retainer ring with the aperture 140 in which it is to be installed.

The assembly of mandrel 200 and punch 198 is then advanced in the arrow 186 direction with the cutting edges 210 and 219 of die 196 and punch 198 severing blank 184 from strip 206 and vacuum system 232 trapping the blank on the upper end segment 218 of the punch in axial alignment with retainer ring 178.

As punch 198 continues through and beyond die 196 in the arrow 186 direction, blank 184 and retainer ring 178 are pressed into aperture 140. This tensions and eliminates distortions in the window-forming portion of the blank and begins the seal-forming deformation of blank 184 by virtue of peripheral blank segment 188 being trapped against the outer edge segment 174 of aperture boundary 164 (FIG. 5). Continued movement of the punch 198 in the arrow 186 direction: (1) completes the formation of the seal 188 in the gap 190 between the boundary of aperture 140 and the periphery of retainer ring 178 and the elimination of distortions in the window-forming material, (2) displaces the window-forming segment 144 of the blank into the above-discussed flush-mounted relationship with the inner, sampling passage-defining surface 156 of airway adapter side wall 160; and (3) snaps retainer 178 into place to positively retain the window in place (see FIG. 6). If blank 184 is fabricated from the preferred material, the seal 188 is formed without wrinkling, creasing, folding, or puckering of the material and without that material being sheared by the retainer. This promotes gastight sealing of the gap 190 between the retainer 178 and the aperture 144 in which it is installed.

Finally, punch 198 and mandrel 200 are retracted to the illustrated position to ready machine 192 for the next installation cycle.

It was pointed out above that there are many cuvettes in which polymeric, infrared radiation transmitting windows may be employed to advantage in accord with the principles of the present invention. One of these is discussed above; and it may be manufactured in different sizes suiting it for adult, neonatal, and other applications. A second such cuvette and the folded path gas analyzer in which it is employed are shown in diagrammatic form in FIGS. 7 and 8 and identified by reference characters 240 and 242, respectively.

Cuvette 242 has top and bottom walls 244 and 246 fabricated of a porous, particulate material trapping polyethylene or other material with sufficient structural integrity and dimensional stability to positively locate with a precise distance therebetween two radiation transmitting windows 248 and 250 embodying the principles of the present invention as elucidated above. These windows may be assembled to cuvette walls 244 and 246 and the gaps between the windows and the walls sealed with retainer rings of the character described above. To this end, recesses 252 and 254 formed in cuvette top and bottom walls 244 and 246 and opening onto the opposite sides 256 and 258 of the cuvette have V-shaped boundaries as discussed above and best shown in FIGS. 5 and 6 which cause the retainer rings 264 and 266 to snap into place as they are pressed into the apertures.

Figure 7:
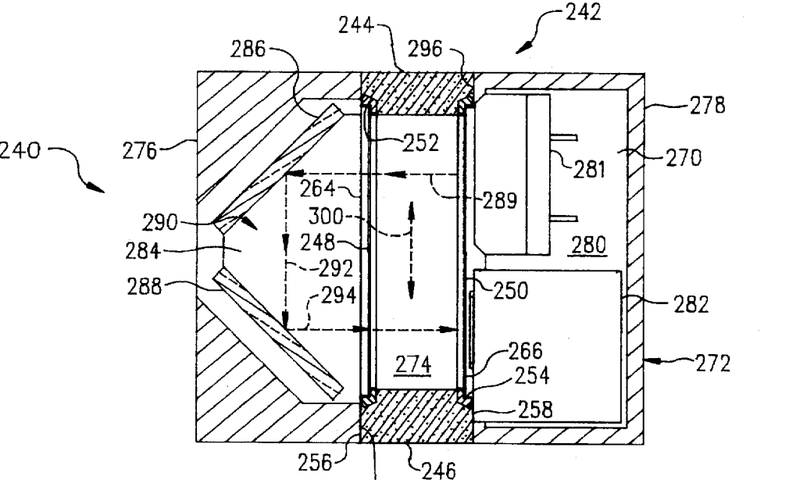
FIG. 7 is a simplified vertical section through a second gas analyzer with a cuvette which also embodies the principle of the present invention.
Figure 8:
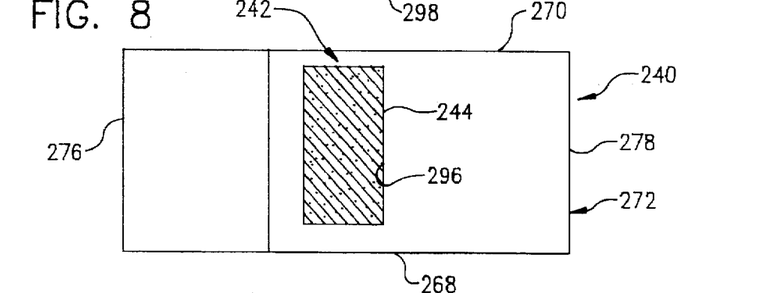
FIG. 8 is a top view of the cuvette of FIG.

Cuvette top and bottom walls 244 and 246, windows 248 and 250, and the side walls 268 and 270 of gas analyzer housing 272 cooperate to define a sampling passage 274 for the gas being monitored.

Cuvette 242 is installed in gas analyzer housing 272 between its left-hand and right-hand ends 276 and 278. Mounted in a thus defined right-hand compartment 280 are an infrared radiation emitter unit 281 and an infrared radiation detector unit 282 which may be of the character shown in FIG. 2 and discussed above. Mounted in a complementary left-hand end compartment 284 are infrared radiation-reflecting mirrors 286 and 288.

Infrared radiation generated by emitter unit 281 is formed into a beam 49 as in the unit 28 depicted in FIG. 2. Beam 49 is propagated along the first leg 289 of an optical path 290 through cuvette window 250, the gas(es) in cuvette sampling passage 274, and cuvette window 248 to mirror 286. The beam of radiation is attenuated as it passes through cuvette 242 to an extent proportional to the concentration of the gas being monitored.

Mirror 286 turns the beam of infrared radiation 90 degrees, causing it to travel along the second leg 292 of optical path 290 to the second of the infrared radiation reflecting mirrors 288. That mirror turns the beam 90 another degrees. This causes the beam to travel along a third optical path leg 294 in a direction opposite to that in which it was initially propagated through: cuvette window 248, the gas(es) in cuvette sampling passage 274, and cuvette window 250 to infrared radiation detector unit 282, the gas again being attenuated to a degree proportional to the concentration of the gas being monitored.

The twice attenuated beam of infrared radiation is intercepted by detector unit 282 which consequentially outputs an electrical signal indicative of the concentration of the monitored gas.

Gas analyzer 240 is designed to monitor gases which reach cuvette 242 through one of the two ports 296 and 298 in gas analyzer casing side walls 268 and 270. These gases enter the sampling passage 274 in cuvette 242 and exit from that passage through the porous cuvette top and bottom walls 246 and 244 as indicated by double-headed arrow 300 in FIG. 7.

This type of gas analyzer can be employed to advantage as one example to monitor gases in rooms, buildings, and other confined spaces. Gas analyzer 240 has the advantage of being compact, and it can be produced at lower cost by virtue of its employing polymeric windows rather than the customary sapphire for transferring infrared radiation into and out of cuvette 242.

Figure 9:
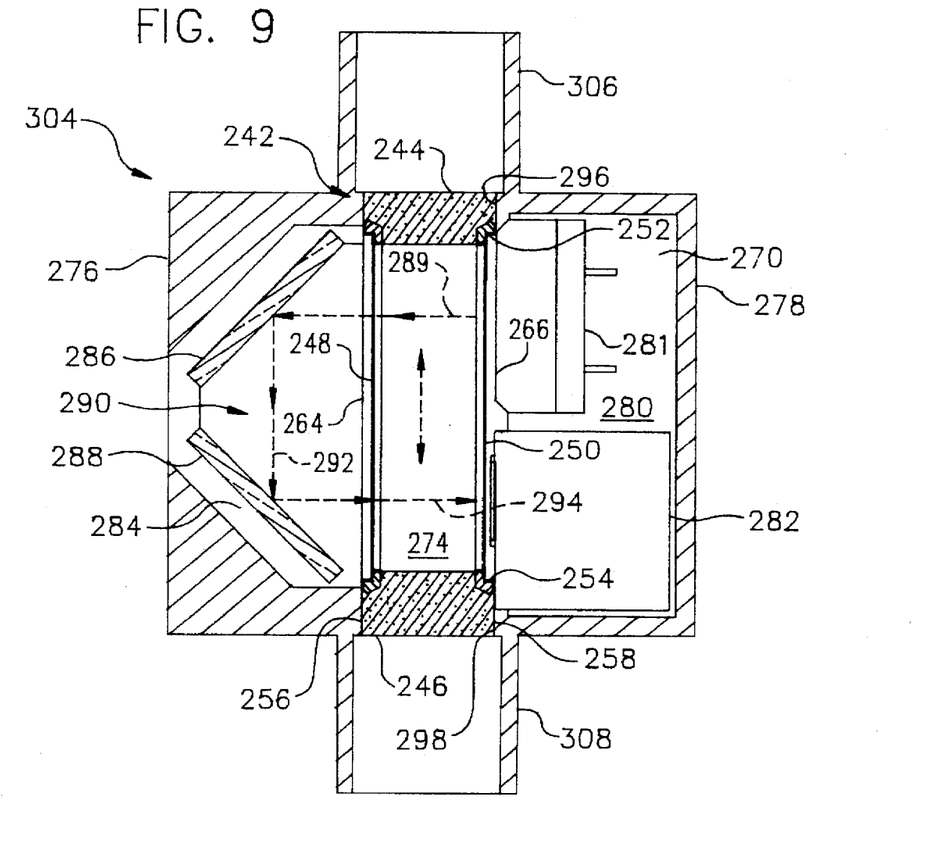
FIG. 9 is a view like FIG. 7 of a third gas analyzer with a cuvette which embodies the principles of the present invention.
Figure 10:
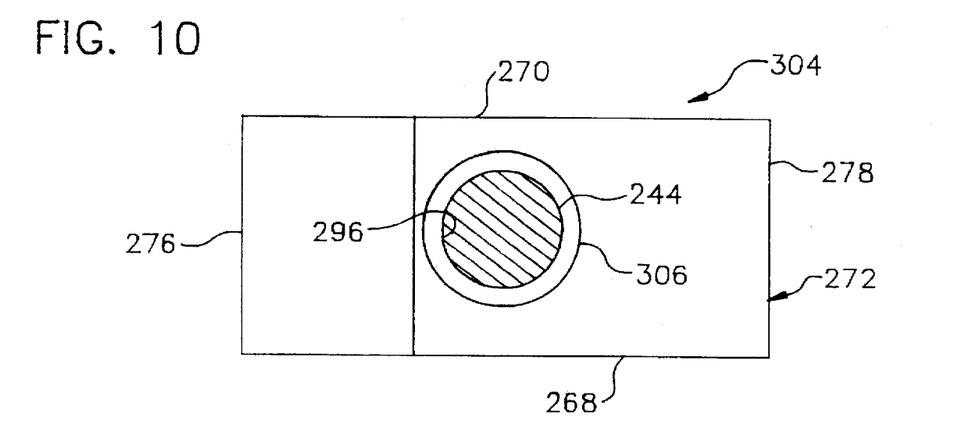
FIG. 10 is a top view of the cuvette shown in FIG. 9.

Referring still to the drawings, FIGS. 9 and 10 depict a folded path gas analyzer 304 which differs from the analyzer 240 just discussed primarily by the addition of tubular fittings 306 and 308. These fittings communicate with ports 296 and 298 in the side walls 268 and 270 of gas analyzer housing 272.

Gas analyzer 304 is employed in medical and other applications where recirculation of the gas(es) introduced into sampling passage 274 is required or advantageous and/or where positive circulation as opposed to convective or diffusive flow of the gas(es) through the sampling chamber is dictated. The compactness and light weight of gas analyzer 304 is particularly beneficial in in-line applications such as end tidal carbon dioxide monitoring because it can be located close to the patient's face, which is out of the way and promotes accuracy.

Cuvettes of the diffusion/convective and positive flow types just described above and illustrated in FIGS. 7–10 can vary considerably from the specific, exemplary configurations shown in the drawings. For example, they may be constructed with a porous, gas transmitting wall which extends all the way around the radiation transmitting windows.

Figure 12:
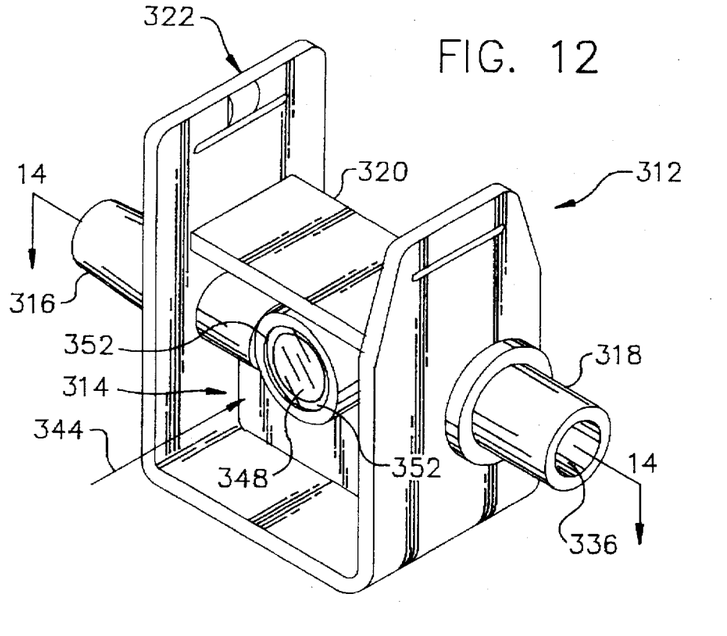
FIG. 12 is a perspective view of a sampling airway adapter employing the principles of the present invention.
Figure 13:
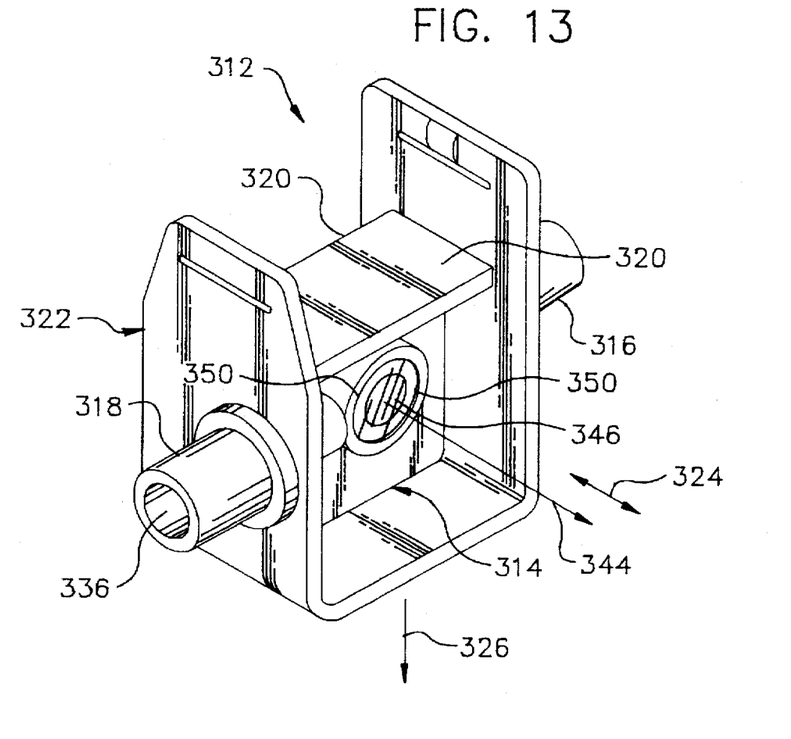
FIG. 13 is a second perspective view of the sampling airway adapter.
Figure 14:
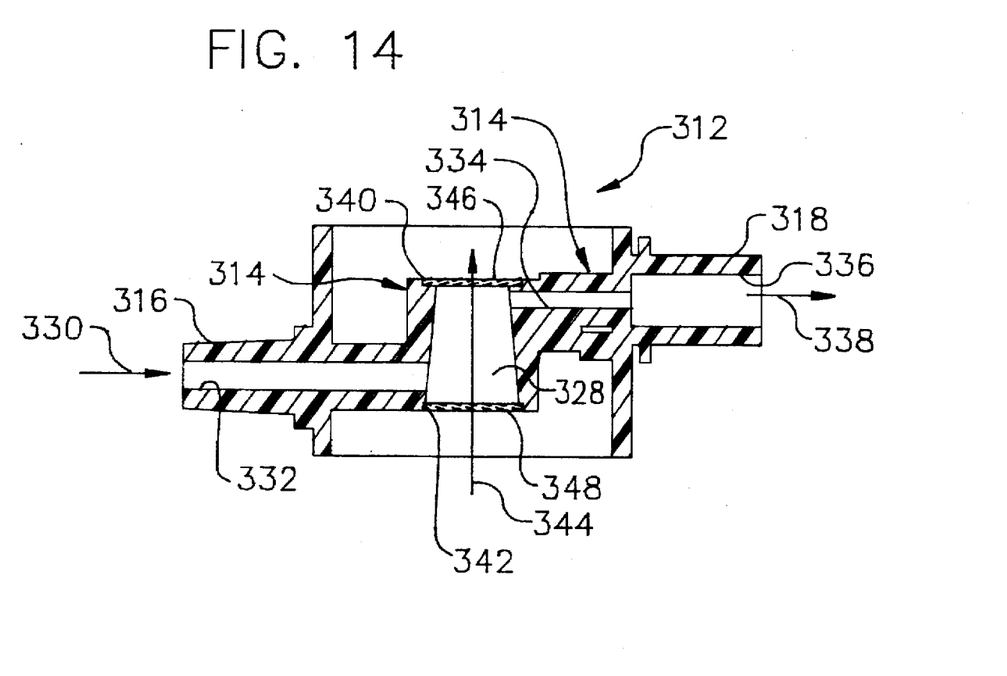
FIG. 14 is a section through FIG. 12 taken substantially along line 14—14 of the latter figure.

Yet another cuvette embodying the principles of the present invention is the sampling airway adapter illustrated in FIGS. 12–14 and identified by reference character 312. The particular adapter depicted in the drawings is molded from a polysulfone. However, it may equally well be manufactured from a polycarbonate or a comparable polymer.

Cuvette 312 has a center section 314 and hollow, cylindrical, left-hand and right-hand end sections 316 and 318. An integral platform 320 of cuvette center section 314 provides a seat for a transducer such as that depicted in FIG. 1 and identified by reference character 24. An integral, U-shaped casing element 322 positively locates the transducer endwise of cuvette 312 and, also in that transverse direction indicated by arrow 324 in FIG. 13. Arrow 326 in the same figure shows the direction in which the transducer is displaced to detachably assembly it to cuvette 312. The airway adapter snaps into place (see the above-cited '858 and '859 patents), and no tools are needed to assemble or remove the adapter.

As is best shown in FIG. 14, a transversely oriented, frustoconically sectioned sampling chamber 328 is formed in the central section 314 of cuvette 312. The gas being sampled flows in the direction indicated by arrow 330 in FIG. 14 through the hollow bore 332 of the cuvette's left-hand end section 316 to the sampling chamber where the concentration of a particular specie such as carbon dioxide is measured, using the non-dispersive infrared radiation technique discussed above. Thereafter, the sample is discharged from chamber 328 through a communicating passage 334 in the central cuvette section 314 and the hollow bore 336 of right-hand cuvette section 318 as suggested by arrow 338.

Apertures 340 and 342 are formed in, and on opposite sides of, the center section 314 of cuvette 312. With a transducer of the type depicted in FIG. 1 assembled to cuvette 312 these apertures are aligned along optical path 344. Thus, infrared radiation outputted from the emitter unit in the transducer can travel in the arrow 344 direction through sampling passage 328 and the gas or gases therein to the detector unit of the transducer.

To: (a) keep the gases in sampling chamber 328 from escaping through apertures 340 and 342 without attenuating the infrared radiation traversing optical path 344, and (b) keep foreign material from the interior of cuvette 312, apertures 340 and 342 are sealed by windows 346 and 348 which have a high transmittance for radiation in the infrared portion of the electromagnetic spectrum. As in the cuvettes discussed above, windows 346 and 348 are fabricated from an appropriate polymer, preferably a biaxially oriented polypropylene. Windows 346 may be formed, installed, and retained in place with skeletal retainers 350 and 352 of the character discussed above or by any other appropriate technique.

The invention may be embodied in many forms without departing from the spirit or essential characteristics of the invention. The present embodiments are therefore to be considered in all respects as illustrative and not restrictive, the scope of the invention being indicated by the appended claims rather than by the foregoing description. All changes which come within the meaning and range of equivalency of the claims are therefore intended to be embraced therein.

What is claimed is:

1. A cuvette which comprises:
   a sampling passage defined by wall means having through apertures which are located on opposite sides of the sampling passage and are aligned along an optical path traversing the sampling passage; and
   windows in said apertures to keep a gas in said passage from escaping through said apertures and to isolate the sampling passage from contaminants in the surrounding environs;

15 each said window being fabricated from a segment of infrared radiation transmitting polymeric film and allowing a beam of radiation originated on one side of said cuvette to traverse the gas in said sampling passage and then be processed on the opposite side of the cuvette;

said cuvette further comprising a retainer ring installed in each said aperture to keep the window therein flat and distortion-free and to immobilize the windows in a parallel, spaced apart relationship with a selected, optical path length therebetween; and each said segment of film having a portion which surrounds the retainer ring and is clamped between the periphery of the retainer ring and the perimeter of the aperture to seal the gap therebetween; and each said retainer ring having a fit with the cuvette wall means around the periphery of the aperture in which said retainer ring is installed that provides window stretching pinch points between the retainer ring and the cuvette around the perimeter of the retainer ring.

2. A cuvette as defined in claim 1 in which the perimeter of each said retainer ring and the perimeter of the aperture in which the retainer ring is installed have complementary configurations such that the retainer ring can be snap-fitted in said cuvette wall means to fix the retainer ring in the aperture.

3. A cuvette as defined in claim 1 in which the window forming polymeric film is under tension.

4. A cuvette as defined in claim 1 in which the ends of the apertures communicating with the sampling passage are sufficiently small to keep the retainer rings and windows from being displaced into said sampling passage.

5. A cuvette as defined in claim 1 in which the film is fabricated from a malleable polymer.

6. A cuvette as defined in claim 1:

which has wall means with an inner surface bounding said sampling passage;

in which said apertures are formed in said wall means; and in which said windows are so located in said apertures that the inner surfaces of the windows are flush with the inner surface of the wall means.

7. A cuvette as defined in claim 1 in which each retainer ring is fabricated from a deformation-and creep-resistant material.

8. A cuvette as defined in claim 1 in which said cuvette wall means has at least one segment which is sufficiently porous for a gas being monitored to pass to and/or from the sampling passage by diffusion or convection.

9. A method of assembling a cuvette which comprises the steps of:

providing a cuvette component having wall means providing a sampling passage and apertures which are located on opposite sides of the sampling passage and aligned along a path traversing the sampling passage: and installing windows in said apertures to keep a gas in said passage from escaping through said apertures and to isolate the sampling passage from contaminants in the surrounding environs;

said windows being fabricated from an infrared radiation transmitting polymer, whereby a beam of infrared radiation originated on one side of said cuvette can traverse the gas in said sampling passage and then be processed on the opposite side of the cuvette; and

16 each said window being installed by:

placing an aperture spanning and overlapping blank fabricated from a polymeric, window-forming, infrared radiation transmitting stock material over an aperture;

providing a retainer ring dimensioned to fit the aperture and to be retained therein with a pinch-point-providing fit between the retainer ring and said wall means around the perimeter of the aperture; and so displacing said retainer ring through said aperture toward said sampling passage as to: (a) pinch said blank between the retainer ring and said wall means around the perimeter of the retainer ring and thereby tension said blank and eliminate distortions that might be present in a window-defining segment of said blank; and (b) displace said window defining segment to and immobilize it at a precisely defined locus in said wall means to provide a flat, accurately located, aperture spanning window with a portion of the blank surrounding the retainer ring and sealing the gap between the perimeter of the retainer ring and the perimeter of the aperture.

10. A method as defined in claim 9 which employs means for installing each said window and the complementary retainer ring which is displaceable toward a complementary aperture in said cuvette housing to press blank and said retainer ring into the complementary aperture and has: a retainer ring receiving recess for aligning said retainer ring with said aperture;

means for cutting said blank from stock material, and vacuum means for holding said blank in alignment with the retainer ring as said blank and said retainer ring are displaced toward said cuvette.

11. A method as defined in claim 10 which includes the step of installing a mandrel in the cuvette sampling passage to align an aperture in the cuvette with the blank and retainer ring and to prevent deformation of the cuvette during installation of the window and the retainer ring.

12. A method as defined in claim 9 in which that end of each aperture communicating with the sampling passage is sufficiently small to keep the retainer ring and window in that aperture from being displaced into said sampling passage during or after the installation of said window and said retainer ring.

13. A method as defined in claim 9 in which the windows are fabricated from a malleable polymer.

14. A method as defined in claim 13 in which the windows are fabricated from a biaxially oriented polypropylene.

15. A method as defined in claim 9 in which:

said wall means has an inner surface bounding said sampling passage; and said windows are so installed in said apertures that the inner surfaces of the windows are flush with the inner surface of the wall means.

16. A method as defined in claim 9 which includes the step of configuring the periphery of each said retainer ring and the boundary of the aperture in which that aperture is installed in a complementary manner which allows the retainer ring to be snapped into place in the cuvette by pressing the retainer ring into the aperture.

17. A method as defined in claim 16 in which each of said apertures has:

an inner segment configured to provide a retainer ring stop for locating the window in that aperture; and an outer, undercut segment for holding said retainer ring against said stop to immobilize said window.

18. A method as defined in claim 9 in which the cuvette has at least one segment which is fabricated from a material that is sufficiently porous for a gas being monitored to pass into and/or out of the sampling passage by diffusion or convection.

19. A method as defined in claim 9 in which said cuvette is fabricated from a rigid, essentially non-deformable material such that the cuvette is by itself capable of maintaining a selected distance between the cuvette windows.

* * * * *